US009540308B2

(12) United States Patent
Matsuo et al.

(10) Patent No.: US 9,540,308 B2
(45) Date of Patent: Jan. 10, 2017

(54) METHOD FOR PRODUCING IRON CARBOXYLATE

(71) Applicant: MITSUBISHI RAYON CO., LTD., Chiyoda-ku (JP)

(72) Inventors: Takeshi Matsuo, Otake (JP); Naoshi Murata, Otake (JP); Hiroyuki Mori, Otake (JP)

(73) Assignee: MITSUBISHI RAYON CO., LTD., Chiyoda-ku (JP)

( * ) Notice: Subject to any disclaimer, the term of this patent is extended or adjusted under 35 U.S.C. 154(b) by 0 days.

(21) Appl. No.: 14/420,490

(22) PCT Filed: Aug. 2, 2013

(86) PCT No.: PCT/JP2013/070970
§ 371 (c)(1),
(2) Date: Feb. 9, 2015

(87) PCT Pub. No.: WO2014/030523
PCT Pub. Date: Feb. 27, 2014

(65) Prior Publication Data
US 2015/0218080 A1    Aug. 6, 2015

(30) Foreign Application Priority Data

Aug. 24, 2012 (JP) ................................. 2012-185128
Dec. 20, 2012 (JP) ................................. 2012-278206
May 22, 2013 (JP) ................................. 2013-107586

(51) Int. Cl.
*C07C 67/26* (2006.01)
*C07C 51/41* (2006.01)
*B01J 31/04* (2006.01)

(52) U.S. Cl.
CPC ............... *C07C 67/26* (2013.01); *B01J 31/04* (2013.01); *C07C 51/41* (2013.01); *C07C 51/418* (2013.01); *B01J 2231/49* (2013.01); *B01J 2531/004* (2013.01)

(58) Field of Classification Search
CPC .......... C07C 51/41; C07C 67/26; C07C 53/10; C07C 57/04; C07C 69/54; C07C 51/418; B01J 2231/49; B01J 2531/004; B01J 31/04
USPC .................... 560/209; 562/598, 607
See application file for complete search history.

(56) References Cited

U.S. PATENT DOCUMENTS

| 8,697,899 B2 * | 4/2014 | Murata ................. C07C 67/26 556/149 |
| 2009/0105493 A1 | 4/2009 | Jang et al. |
| 2009/0209783 A1 * | 8/2009 | Curtis ................... C07C 67/26 560/218 |
| 2013/0172591 A1 | 7/2013 | Murata et al. |

FOREIGN PATENT DOCUMENTS

| JP | 49-76816 A | 7/1974 |
| JP | 49-82623 A | 8/1974 |
| JP | 57-175141 A | 10/1982 |
| JP | 07-017896 A | 1/1995 |
| JP | 2008-201780 A | 9/2008 |
| KR | 2003-0095328 A | 12/2003 |
| RU | 2292330 * | 1/2007 |
| RU | 2314285 * | 1/2008 |
| WO | WO 2012/090905 A1 | 7/2012 |

OTHER PUBLICATIONS

Machine generated translation of RU 2314285, p. 1-9, obtained Mar. 31, 2016.*
Machine generated translation of RU 2292330, p. 1-8, obtained Mar. 31, 2016.*
English language translation of RU 2314285, p. 1-14, dated Apr. 2016.*
English language translation of RU 2292330, p. 1-14, dated Apr. 2016.*
International Search Report issued Nov. 5, 2013 in PCT/JP2013/070970 Filed Aug. 2, 2013.
A. M. Ivaron, et al., "Method for production of ferric (II) formate in aqueous medium", Chemical Abstracts, vol. 146, No. 9, 2007, p. 1273.
James K. McCusker, et al., "Spin frustration: A hexanuclear ferric complex with a S = 5 ground state", J. Am. Chem. Soc., vol. 113, 1991, pp. 6114-6124.
Extended European Search Report issued Jul. 7, 2015 in Patent Application No. 13830779.8.

* cited by examiner

*Primary Examiner* — Jafar Parsa
*Assistant Examiner* — Amy C Bonaparte
(74) *Attorney, Agent, or Firm* — Oblon, McClelland, Maier & Neustadt, L.L.P.

(57) ABSTRACT

Method for producing an iron carboxylate, whereby it becomes possible to prevent the generation of hydrogen during the production of the iron carboxylate by the reaction of a carboxylic acid with metal iron. An embodiment of the present invention is a method for producing an iron carboxylate by reacting metal iron with a carboxylic acid in a reaction solution, wherein the reaction solution contains a non-iron metal having a standard electrode potential of −2.5 to 0.1 inclusive or a metal compound containing the metal, or the reaction solution contains at least one metal selected from the group consisting of Ag, Bi and Pd or a metal compound containing the metal.

16 Claims, No Drawings

METHOD FOR PRODUCING IRON CARBOXYLATE

TECHNICAL FIELD

The present invention relates to a method for producing an iron carboxylate.

BACKGROUND ART

Several methods have been suggested as the method for producing an iron carboxylate (for example, Non-Patent Document 1 and Patent Document 1). These methods use iron salt compounds such as iron chloride and iron nitrate as raw materials. Furthermore, other methods include methods of dissolving metal powders in carboxylic acids (Patent Documents 2 and 3). In the iron carboxylates prepared by these other methods, since ion species of halogens and the like do not exist in large amounts with respect to iron, iron carboxylates of high purity can be obtained.

CITATION LIST

Patent Document

Patent Document 1: JP 7-17896 A
Patent Document 2: JP 57-175141 A
Patent Document 3: JP 2008-201780 A

Non-Patent Document

Non-Patent Document 1: J. Am. Chem. Soc., 1991, 113, 6114

DISCLOSURE OF THE INVENTION

Problem to be Solved by the Invention

In a method of causing a metal powder to react with an acid as described in Patent Document 2 or 3, it is known that hydrogen is generated, and hydrogen is generated even in a reaction between a carboxylic acid and metal iron. Therefore, it is desired to develop a means for reducing the generation of hydrogen.

Thus, it is an object of the present invention to provide a method for producing an iron carboxylate in which when an iron carboxylate is obtained by causing a carboxylic acid to react with metal iron, generation of hydrogen can be suppressed.

Means for Solving Problem

According to an aspect of the present invention, there is provided a method for producing an iron carboxylate by causing metal iron to react with a carboxylic acid in a reaction liquid, in which a trivalent iron compound is added to the reaction liquid; the reaction liquid contains a trivalent iron compound at the time of initiation of the reaction; the reaction liquid contains a metal other than iron having a standard electrode potential of from −2.5 to 0.1, or a metal compound containing the relevant metal; or the reaction liquid contains at least one metal selected from the group consisting of Ag, Bi and Pd, or a metal compound containing the relevant metal.

Furthermore, according to another aspect of the present invention, there is provided a method for producing an iron carboxylate by causing metal iron to react with a carboxylic acid in a reaction liquid, in which the reaction liquid satisfies the following conditions (B) and (C):

(B) a reaction liquid in which the content of a Cu compound is such that the amount of Cu contained in the Cu compound is from 0.00001 moles to 5 moles relative to 1 mole of the metal iron;

(C) a reaction liquid containing an anion that satisfies the following condition (D), in an amount in the range of from 0.0001 moles to 10 moles relative to 1 mole of the metal iron; and (D) an anion whose protonated form has a pKa (negative common logarithm of the acid dissociation constant) in water (25° C.) of 2 or less.

Furthermore, according to another aspect of the present invention, there is provided a method for producing a carboxylic acid hydroxyalkyl ester by causing an alkylene oxide to react with a carboxylic acid, the method including using an iron carboxylate produced by the method described above as a catalyst.

Effect of the Invention

According to the present invention, an iron carboxylate can be produced while generation of hydrogen is suppressed.

MODE(S) FOR CARRYING OUT THE INVENTION

The method for producing an iron carboxylate of the present exemplary embodiment is explained in detail below, but the scope of the present invention is not limited by these explanations, and in addition to the following examples, any embodiment can be carried out appropriately to the extent that the purport of the present invention is not impaired.

Metal iron as a raw material of the iron carboxylate is not particularly limited but from the viewpoint of solubility, powdered iron, that is, so-called iron powder is preferred. The particle size of the iron powder is not particularly limited; however, from the viewpoints of solubility and safety, the particle size as the median diameter is preferably 0.1 tam or more, more preferably 1 µm or more, even more preferably 10 m or more, and particularly preferably 30 µm or more. Furthermore, the particle size of the iron powder as the median diameter is preferably 3000 µm or less, more preferably 1000 µm or less, even more preferably 500 µm or less, and particularly preferably 300 m or less. The kind of the iron powder is not particularly limited, but examples include atomized iron powder, reduced iron powder, and electrolytic iron powder.

There are no particular limitations on the kind of the carboxylic acid used in the present exemplary embodiment. The number of carboxyl groups in the molecule of the carboxylic acid may be one or two or more. Also, the carboxylic acid may have one or more of a double bond, a triple bond, an ester bond, an amide bond, an ether bond, a sulfide bond, a disulfide bond, a urethane bond, an amino group, a nitro group, a cyano group, a thiol group, a hydroxyl group, a ketone group, a formyl group, an acetal group, a thioacetal group, a sulfonyl group, halogen, silicon, phosphorus, and the like in the molecule, or may have a cyclic structure or an aromatic structure. The carboxylic acid is preferably a carboxylic acid selected from the group consisting of formic acid, acetic acid, propionic acid, butyric acid, oxalic acid, malonic acid, succinic acid, glutaric acid, adipic acid, fumaric acid, maleic acid, pyruvic acid, acrylic acid, methacrylic acid, and crotonic acid. The carboxylic acid is more preferably a carboxylic acid selected from the group consisting of acetic acid, acrylic acid, and methacrylic acid, and is even more preferably acrylic acid or methacrylic acid. The carboxylic acids may be used singly, or may be used in combination of two or more kinds.

Among the carboxylic acids used in the present exemplary embodiment, the amount of a carboxylic acid having n carboxylic groups (wherein n represents an integer of 1 or larger) in one molecule is not particularly limited, but the amount is preferably 1/n moles or more, more preferably 2/n moles or more, even more preferably 2.5/n moles or more, and particularly preferably 5/n moles or more, relative to 1 mole of metal iron. Furthermore, the amount of the carboxylic acid is preferably 1,000,000/n moles or less, more preferably 100,000/n moles or less, even more preferably 10,000/n moles or less, and particularly preferably 1000/n moles or less, relative to 1 mole of the metal iron. When the amount of the carboxylic acid is 1/n moles or more relative to 1 mole of the metal iron, the amount of unreacted metal iron can be reduced. Furthermore, when the amount of the carboxylic acid is 1,000,000/n moles or less relative to 1 mole of the metal iron, the cost for heating and the like can be reduced, and an iron carboxylate can be produced economically efficiently.

When the carboxylic acid has a double bond, it is preferable to blow in oxygen or an oxygen-containing gas such as air for the purpose of preventing polymerization when a mixture of metal iron and the carboxylic acid is heated to react. Also, it is preferable to add a polymerization inhibitor to the mixture and then carry out a heating treatment in the co-presence of the polymerization inhibitor. There are no particular limitations on the polymerization inhibitor, but examples thereof include hydroquinone; phenolic compounds such as para-methoxyphenol; amine-based compounds such as N,N'-diisopropyl-para-phenylenediamine, N,N'-di-2-naphthyl-para-phenylenediamine, N-phenyl-N-(1,3-dimethylbutyl)-para-phenylenediamine, and phenothiazine; N-oxyl-based compounds such as 4-hydroxy-2,2,6,6-tetramethylpiperidine-N-oxyl and 4-benzoyloxy-2,2,6,6-tetramethylpiperidine-N-oxyl; and N-oxyl-based compounds exemplified by the following Formula (1). The polymerization inhibitors may be used singly, or may be used in combination of two or more kinds.

[Chemical Formula 1]

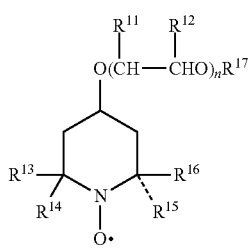

(1)

wherein in Formula (1), n represents 1 to 18; $R^{11}$ and $R^{12}$ both represent hydrogen atoms, or one of them represents a hydrogen atom while the other represents a methyl group; $R^{13}$, $R^{14}$, $R^{15}$ and $R^{16}$ each represent a linear or branched alkyl group; and $R^{17}$ represents a hydrogen atom or an acyl group having a linear, branched or cyclic hydrocarbon group.

Examples of $R^{17}$ of Formula (1) include an acetyl group, a benzoyl group, an acryloyl group, and a methacryloyl group. In Formula (1), $R^{11}$ and $R^{12}$ may be each independently bonded to different carbon atoms.

The range of the reaction temperature at the time of heating a mixture of metal iron and a carboxylic acid to react is preferably 50 to 250° C., more preferably 60 to 200° C., and even more preferably 80 to 150° C. When the reaction temperature is 50° C. or higher, the reaction is accelerated, which is preferable. On the other hand, when the reaction temperature is 250° C. or lower, it is preferable because less side products are generated, and decomposition of the raw material carboxylic acid is suppressed. Meanwhile, the heating temperature is not necessarily constant and may vary within a preferred range.

When the mixture of metal iron and a carboxylic acid is heated to react, it is preferable to heat treat the mixture at a temperature in the range of 50 to 250° C. for 0.1 to 80 hours. When the mixture is allowed to react for 0.1 hours or longer, metal iron can be sufficiently dissolved. Furthermore, when the mixture is allowed to react for 80 hours or shorter, an iron carboxylate can be satisfactorily produced from the viewpoint of economic efficiency such as the process cost. In a case in which a carboxylic acid having a double bond is used as a raw material, the range of the time for heating and reacting is preferably 0.1 to 50 hours, more preferably 0.3 to 30 hours, even more preferably 0.5 to 20 hours, and particularly preferably 1 to 15 hours. When a carboxylic acid having a double bond is used as a raw material, polymerization of the carboxylic acid can be suppressed by heating the mixture to react for 50 hours or shorter.

The reaction liquid containing a carboxylic acid and metal iron may include a solvent. There are no limitations on the kind and amount of the solvent. Examples of the solvent include water and organic compounds having 1 to 25 carbon atoms. The solvent may have one or more of a double bond, a triple bond, an ester bond, an amide bond, an ether bond, a sulfide bond, a disulfide bond, a urethane bond, an amino group, a nitro group, a cyano group, a hydroxyl group, a thiol group, a hydroxyl group, a ketone group, a formyl group, an acetal group, a thioacetal group, a sulfonyl group, halogen, silicon, phosphorus, and the like. Furthermore, the solvent may have a cyclic structure or an aromatic structure, or may have an ionic bond. Examples of the solvent other than water include benzene, toluene, xylene, n-hexane, cyclohexane, n-heptane, n-octane, n-nonane, n-decane, methanol, ethanol, 1-propanol, 2-propanol, 1-butanol, 2-butanol, isobutyl alcohol, 1-pentanol, isoamyl alcohol, sec-amyl alcohol, tert-amyl alcohol, neopentyl alcohol, 1-hexanol, cyclohexanol, 1-heptanol, 2-methylcyclohexanol, 1-octaol, 2-ethylhexanol, 1-nonanol, 1-decanol, phenol, o-cresol, m-cresol, p-cresol, 2,6-xylenol, ethylene glycol, 1,2-propanediol, 1,3-propanediol, 1,2-butanediol, 1,3-butanediol, 1,4-butanediol, 1,6-hexanediol, diethylene glycol, triethylene glycol, tetraethylene glycol, 1,4-dioxane, tetrahydrofuran, tetrahydropyran, anisole, methyl tert-butyl ether, dibutyl ether, diphenyl ether, ethylene glycol monomethyl ether, ethylene glycol monoethyl ether, ethylene glycol mono-n-butyl ether, acetone, methyl ethyl ketone, methyl n-butyl ketone, methyl isobutyl ketone, cyclohexanone, 2-methylcyclohexanone, 2-hydroxyethyl acrylate, 2-hydroxyethyl methacrylate, 2-hydroxypropyl acrylate, 2-hydroxypropyl methacrylate, 2-hydroxy-1-methylethyl acrylate, 2-hydroxy-1-methylethyl methacrylate, diethylene glycol monoacrylate, diethylene glycol monomethacrylate, triethylene glycol monoacrylate, triethylene glycol monomethacrylate, ethylene glycol diacrylate, ethylene glycol dimethacrylate, diethylene glycol diacrylate, diethylene glycol dimethacrylate, 1,2-propylene glycol diacrylate, and 1,2-propylene glycol dimethacrylate. Also, the solvents may be used singly, or may be used in combination of two or more kinds thereof.

The trivalent iron compound used in the present exemplary embodiment may contain divalent iron (Fe(II)) or other metals in the molecule, and there are no particular limitations thereon. Examples of the trivalent iron compound include $Fe(acac)_3$, iron(III) formate, iron(III) acetate, iron(III) propionate, iron(III) butyrate, iron(III) acrylate, iron (III) methacrylate, iron(III) oxide, triferric tetraoxide, iron(III) oxyhydroxide, iron(III) sulfate, iron(III) citrate, iron(III) nitrate, iron(III) chloride, iron(III) bromide, iron (III) iodide, iron(III) sulfate, iron(III) phosphate, an iron (III)-ethylenediamine tetraacetate complex, and an iron(III)-ethylenediamine-N,N'-disuccinic acid complex. Hydrates, amine adducts and the like of the trivalent iron compounds listed as examples can also be used. Among the trivalent iron compounds listed as examples, $Fe(acac)_3$, iron(III) acetate, iron(III) oxide, triferric tetraoxide, iron(III) acrylate, and iron(III) methacrylate are preferred; $Fe(acac)_3$, iron(III) acetate, iron(III) acrylate, and iron(III) methacrylate are more preferred; and iron(III) acrylate or iron(III) methacrylate is even more preferred. The trivalent iron compounds may be used singly, or may be used in combination of two or more kinds. Also, these may be used in combination with Fe(II) compounds or zero-valent iron compounds.

There are no particular limitations on the amount of addition of the trivalent iron compound used in the present exemplary embodiment or the content of the trivalent iron compound at the time of initiation of the reaction in the reaction liquid; however, from the viewpoints of economic efficiency and the purity of the product, the amount or content is preferably from 0.0001 moles to 50 moles in terms of trivalent iron relative to 1 mole of metal iron. In other words, the amount of addition of the trivalent iron compound is preferably an amount such that the amount of trivalent iron contained in the trivalent iron compound is from 0.0001 moles to 50 moles relative to 1 mole of metal iron. Furthermore, the amount of addition of the trivalent iron compound is more preferably 0.001 moles or more, even more preferably 0.005 moles or more, particularly preferably 0.01 moles or more, and most preferably 0.05 moles or more, in terms of trivalent iron relative to 1 mole of the metal iron. Furthermore, the amount of addition of the trivalent iron compound is more preferably 10 moles or less, even more preferably 5 moles or less, particularly preferably 1 mole or less, and most preferably 0.5 moles or less, in terms of trivalent iron relative to 1 mole of the metal iron. When the amount of addition in terms of trivalent iron is 0.0001 moles or more relative to 1 mole of the metal iron, the influence of impurities on the deactivation of the trivalent iron compound can be suppressed. Furthermore, when the amount of addition in terms of trivalent iron is 50 moles or less relative to 1 mole of the metal iron, a decrease in the productivity of the iron carboxylate or a decrease in the purity of the product can be prevented.

The timing for adding the trivalent iron compound in the present exemplary embodiment may be before the temperature increase of the reaction liquid, or may be in the middle of the reaction after heating; however, since hydrogen is generated even during the temperature increase, it is preferable to add the iron compound in a low temperature state, and it is more preferable to add the iron compound before the initiation of the temperature increase. Furthermore, when the trivalent iron compound is added, the order of introducing the carboxylic acid, metal iron, and trivalent iron compound into the reaction vessel is not particularly limited.

Furthermore, the trivalent iron compound may be added in two or more divided portions, or may be added continuously. Also, the trivalent iron compound may be added after the carboxylic acid or metal iron is mixed with a solvent. In addition, the reaction liquid may be in a state of containing the trivalent iron compound at the time of initiation of the reaction. The trivalent iron compound may be in a state of being dissolved in the reaction liquid, or may be in a state of not being dissolved; however, it is preferable that the iron compound is in a dissolved state.

According to an exemplary embodiment of the present invention, the reaction liquid containing metal iron and a carboxylic acid includes a metal other than iron having a standard electrode potential of from −2.5 to 0.1, or a metal compound containing the relevant metal. That is, according to the present exemplary embodiment, a metal other than iron having a standard electrode potential of from −2.5 to 0.1, or a metal compound containing the relevant metal is introduced into the reaction liquid, and the metal iron and the carboxylic acid are allowed to react therein. The metal compound contains one or more metals other than iron in the molecule.

According to the present specification, the standard electrode potential refers to the standard electrode potential from a zero-valent metal to a metal ion in an aqueous solution at 25° C. and 1 atmosphere, that is, the standard electrode potential of a simple metal in an aqueous solution at 25° C. and 1 atmosphere.

Examples of the metal other than iron having a standard electrode potential of from −2.5 to 0.1 include Be, Mg, Al, Sc, Ti, V, Cr, Mn, Co, Ni, Zn, Ga, Y, Zr, Nb, Mo, Cd, In, Sn, Ta, Ce, Pr, Nd, Sm, Eu, Gd, Tb, Dy, Ho, Er, Tm, Yb, Lu, Hf, Ta, Tl, and Pb. The standard electrode potential is preferably from −1.7 to 0.1, and examples of the metal having the standard electrode potential in that range include Be, Al, Ti, V, Cr, Mn, Co, Ni, Zn, Ga, Zr, Nb, Mo, Cd, In, Sn, Ta, Tl, and Pb. Furthermore, the standard electrode potential is more preferably from −1.2 to 0, and examples of the metal having the standard electrode potential in that range include V, Cr, Mn, Co, Ni, Zn, Ga, Nb, Mo, Cd, In, Sn, Ta, Tl, and Pb. Furthermore, the standard electrode potential is even more preferably from −0.8 to 0, and examples of the metal having the standard electrode potential in that range include Cr, Co, Ni, Ga, Mo, Cd, In, Sn, Tl, and Pb. Also, the standard electrode potential is particularly preferably from −0.44 to 0, and examples of the metal having the standard electrode potential in that range include Co, Ni, Mo, Cd, In, Sn, Tl, and Pb. The standard electrode potential is most preferably from −0.3 to −0.1, and examples of the metal having the standard electrode potential in that range include Co, Ni, Mo, Sn, and Pb. Meanwhile, in a case in which one metal has a number of standard electrode potentials, the standard electrode potential having the smallest value is designated as the standard electrode potential according to the present specification.

According to the present exemplary embodiment, when the standard electrode potential of the metal is −2.5 or higher, generation of hydrogen can be effectively suppressed. Furthermore, when the standard electrode potential of the metal is 0.1 or lower, an iron carboxylate can be produced while inhibition of reaction is suppressed. The standard electrode potentials of metals are described in, for example, "Denki Kagaku Binran (Handbook of Electrochemistry), $4^{th}$ Edition", edited by the Electrochemical Society of Japan (1985), published by Maruzen Co., Ltd. and the like.

The content of the metal other than iron having a standard electrode potential of from −2.5 to 0.1 in the reaction liquid is not particularly limited; however, from the viewpoints of economic efficiency and the purity of the product, the content is preferably from 0.00001 moles to 5 moles relative to 1 mole of the metal iron. Furthermore, the content of the metal compound containing the metal other than iron having a standard electrode potential of from −2.5 to 0.1 is preferably an amount such that the amount of the metal contained in the metal compound is from 0.00001 moles to 5 moles relative to 1 mole of the metal iron.

Furthermore, the content of the metal is more preferably 0.00005 moles or more, more preferably 0.0001 moles or more, particularly preferably 0.0005 moles or more, and most preferably 0.001 moles or more, relative to 1 mole of the metal iron. Furthermore, the content of the metal compound containing the metal other than iron having a standard electrode potential of from −2.5 to 0.1 in the reaction liquid is more preferably an amount such that the amount of the metal contained in the metal compound is 0.00005 moles or more, even more preferably 0.0001 moles or more, particularly preferably 0.0005 moles or more, and most preferably 0.001 moles or more, relative to 1 mole of the metal iron. Furthermore, the content of the metal other than iron having a standard electrode potential of from −2.5 to 0.1 is more preferably 1 mole or less, more preferably 0.5 moles or less, even more preferably 0.05 moles or less, particularly preferably 0.01 moles or less, and most preferably 0.005 moles or less, relative to 1 mole of the metal iron. Furthermore, the content of the metal compound containing the metal other than iron having a standard electrode potential of from −2.5 to 0.1 is more preferably an amount such that the amount of the metal contained in the metal compound is 1 mole or less, even more preferably 0.5 moles or less, still more preferably 0.05 moles or less, particularly preferably 0.01 moles or less, and most preferably 0.005 moles or less, relative to 1 mole of the metal iron. When the content of such a metal is 0.00001 moles or more relative to 1 mole of the metal iron, the influence of impurities on the deactivation of the metal can be effectively suppressed. Also, when the content of such a metal is 5 moles or less relative to 1 mole of the metal iron, a decrease in the productivity of the iron carboxylate or a decrease in the purity of the product can be effectively prevented.

The metal other than iron having a standard electrode potential of from −2.5 to 0.1, or the metal compound containing the metal used in the present exemplary embodiment may be in a state of being dissolved in the reaction liquid, or may be in a state of not being dissolved; however, a dissolved state is preferred.

There are no particular limitations on the metal compound containing the metal other than iron having a standard electrode potential of from −2.5 to 0.1 used in the present exemplary embodiment; however, it is preferable that the metal compound is a compound containing one kind of metal. The metal compound used in the present exemplary embodiment is preferably a compound having the metal and a ligand. The ligand is preferably an ionic ligand, more preferably an ionic ligand formed from an organic molecule, and even more preferably a carboxylate anion ligand. Particularly, the metal compound according to the present exemplary embodiment is preferably an organometallic compound having a metal and an ionic ligand.

Examples of the ligand include acetate ion, methacrylate ion, acrylate ion, acetylacetonate ion, formate ion, propionate ion, butyrate ion, oxalate ion, malonate ion, succinate ion, glutarate ion, adipate ion, fumarate ion, maleate ion, pyruvate ion, crotonate ion, and citrate ion.

Examples of the organometallic compound include tin acetate, tin methacrylate, tin acrylate, tin acetylacetonate, nickel acetate, nickel methacrylate, nickel acrylate, nickel acetylacetonate, chromium acetate, chromium methacrylate, chromium acrylate, manganese acetate, manganese methacrylate, manganese acrylate, manganese acetylacetonate, lead acetate, lead methacrylate, lead acrylate, lead acetylacetonate, molybdenum acetate, molybdenum methacrylate, molybdenum acrylate, bis(acetylacetonato)molybdenum dioxide, bis(methacrylato)molybdenum dioxide, cobalt acetate, cobalt methacrylate, cobalt acrylate, and cobalt acetylacetonate. In addition to them, hydrates and amine adducts of these metal compounds may also be included.

According to an exemplary embodiment of the present invention, the reaction liquid containing metal iron and a carboxylic acid includes at least one metal selected from the group consisting of Ag, Bi and Pd, or a metal compound containing the relevant metal. That is, according to an exemplary embodiment of the present invention, at least one metal selected from the group consisting of Ag, Bi and Pd, or a compound containing the metal is introduced into the reaction liquid, and the metal iron and the carboxylic acid are allowed to react therein.

The at least one metal selected from the group consisting of Ag, Bi and Pd, or the metal compound containing the relevant metal is preferably at least one metal selected from the group consisting of Bi and Pd, or a metal compound containing the relevant metal, and is particularly preferably Pd or a Pd compound.

There are no particular limitations on the content of the at least one metal selected from the group consisting of Ag, Bi and Pd in the reaction liquid; however, from the viewpoints of economic efficiency and the purity of the product, the content is preferably from 0.00001 moles to 5 moles relative to 1 mole of the metal iron. The content of the metal compound containing at least one metal selected from the group consisting of Ag, Bi and Pd is preferably an amount such that the amount of the metal contained in the metal compound is from 0.00001 moles to 5 moles relative to 1 mole of the metal iron.

Furthermore, the content of the metal is more preferably 0.00005 moles or more, even more preferably 0.0001 moles or more, particularly preferably 0.0005 moles or more, and most preferably 0.001 moles or more, relative to 1 mole of the metal iron.

Furthermore, the content of the metal compound containing at least one metal selected from the group consisting of Ag, Bi and Pd in the reaction liquid is more preferably an amount such that the amount of the metal contained in the metal compound is 0.00005 moles or more, even more preferably 0.0001 moles or more, particularly preferably 0.0005 moles or more, and most preferably 0.001 moles or more, relative to 1 mole of the metal iron.

Furthermore, the content of the at least one metal selected from the group consisting of Ag, Bi and Pd is more preferably 1 mole or less, even more preferably 0.5 moles or less, still more preferably 0.05 moles or less, particularly preferably 0.01 moles or less, and most preferably 0.005 moles or less, relative to 1 mole of the metal iron.

Furthermore, the content of the metal compound containing at least one metal selected from the group consisting of Ag, Bi and Pd is more preferably an amount such that the amount of the metal contained in the metal compound is 1 mole or less, even more preferably 0.5 moles or less, still more preferably 0.05 moles or less, particularly preferably 0.01 moles or less, and most preferably 0.005 moles or less, relative to 1 mole of the metal iron.

When the content of such a metal is 0.00001 moles or more relative to 1 mole of the metal iron, the influence of impurities on the deactivation of the metal can be effectively suppressed. Furthermore, when the content of such a metal is 5 moles or less relative to 1 mole of the metal iron, a decrease in the productivity of the iron carboxylate or the purity of the product can be effectively prevented.

The at least one metal selected from the group consisting of Ag, Bi and Pd, or the metal compound containing the relevant metal used in an exemplary embodiment of the present invention may be in a state of being dissolved in the reaction liquid, or may be in a state of not being dissolved; however, a dissolved state is preferred.

There are no particular limitations on the metal compound containing at least one metal selected from the group consisting of Ag, Bi and Pd used in an exemplary embodiment of the present invention; however, the metal compound is preferably a compound containing one kind of metal. The metal compound containing at least one metal selected from the group consisting of Ag, Bi and Pd used in an exemplary embodiment of the present invention is preferably a compound having the metal and a ligand. The ligand is preferably an ionic ligand, more preferably an ionic ligand formed from an organic molecule, and even more preferably a carboxylate anion ligand. Particularly, the metal compound containing at least one metal selected from the group consisting of Ag, Bi and Pd according to an exemplary embodiment of the present invention is preferably an organometallic compound having a metal and an ionic ligand.

Examples of the ligand include acetate ion, methacrylate ion, acrylate ion, acetylacetonate ion, formate ion, propionate ion, butyrate ion, 2-ethylhexanoate ion, oxalate ion, malonate ion, succinate ion, glutarate ion, adipate ion, fumarate ion, maleate ion, pyruvate ion, crotonate ion, citrate ion, and salicylate ion.

Examples of the organometallic compound include palladium acetate, palladium methacrylate, palladium acrylate, palladium acetylacetonate, tetrakis(triphenylphosphine)palladium, silver acetate, silver methacrylate, silver acrylate, bismuth acetate, bismuth methacrylate, bismuth acrylate, bismuth 2-ethylhexanoate, bismuth acetate oxide, bismuth methacrylate oxide, and bismuth acrylate oxide. In addition to them, hydrates and amine adducts of these metal compounds may also be included.

According to an exemplary embodiment of the present invention, in a case in which a compound containing a metal other than iron having a standard electrode potential of from −2.5 to 0.1 or a metal compound containing the relevant metal is introduced into the reaction liquid, and metal iron and a carboxylic acid are allowed to react, or in a case in which at least one metal selected from the group consisting of Ag, Bi and Pd or a compound containing the relevant metal is introduced into the reaction liquid, and metal iron and a carboxylic acid are allowed to react, it is preferable that the total amount of the anion that is included in the reaction liquid containing the carboxylic acid, metal iron and the like and satisfies the following condition (A) is 10 moles or less relative to 1 mole of the metal iron in the reaction liquid:

(A) an anion whose protonated form has a pKa (negative common logarithm of the acid dissociation constant) in water (25° C.) of 2 or less.

Examples of the anion that satisfies the condition (A) include I⁻, Br⁻, Cl⁻, sulfate ion, nitrate ion, trifluoromethanesulfonate ion, trifluoroacetate ion, maleate ion, and oxalate ion. The pKa according to the condition (A) of trifluoroacetate ion or the like is 1 or less, which is more preferred; the pKa of nitrate ion or the like is 0 or less, which is particularly preferred; and the pKa of I⁻, Br⁻, Cl⁻, sulfate ion, trifluoromethanesulfonate ion or the like is −2 or less, which is most preferred. Meanwhile, when a protonated form has plural pKa values for one compound, the smallest pKa among them is designated as the pKa according to the condition (A). Descriptions on pKa are given in, for example, "LANGE'S HANDBOOK OF CHEMISTRY, 13$^{TH}$ EDITION", written by John A. Dean (1972) (McGraw-Hill Book Company), and the like.

Furthermore, the total amount of the anion that satisfies the condition (A) among the anions included in the reaction liquid is more preferably 1 mole or less, even more preferably 0.1 moles or less, still more preferably 0.01 moles or less, particularly preferably 0.001 moles or less, and most preferably 0.0001 moles or less, relative to 1 mole of the metal iron. When the total amount of the anion that satisfies the condition (A) included in the reaction liquid is 10 moles or less relative to 1 mole of the metal iron, the amount of the protonated form of the anion generated by an equilibrium reaction between the anion and the carboxylic acid is reduced, and generation of hydrogen can be suppressed.

According to an exemplary embodiment of the present invention, in a case in which a Cu compound is introduced into the reaction liquid, and metal iron and a carboxylic acid are allowed to react therein, the reaction liquid containing the carboxylic acid, metal iron and the like satisfies the following conditions (B) and (C):

(B) a reaction liquid in which the content of the Cu compound is an amount such that the amount of Cu contained in the Cu compound is from 0.00001 moles to 5 moles relative to 1 mole of the metal iron;

(C) a reaction liquid containing an anion that satisfies the following condition (D) in an amount in the range of from 0.0001 moles to 10 moles relative to 1 mole of the metal iron; and (D) an anion whose protonated form has a pKa (negative common logarithm of the acid dissociation constant) in water (25° C.) of 2 or less.

The content of the Cu compound in the reaction liquid is more preferably an amount such that the amount of Cu contained in the Cu compound is 0.00005 moles or more, even more preferably 0.0001 moles or more, particularly preferably 0.0005 moles or more, and most preferably 0.001 moles or more, relative to 1 mole of the metal iron.

The content of the Cu compound is more preferably an amount such that the amount of Cu contained in the Cu compound is 1 mole or less, even more preferably 0.5 moles or less, still more preferably 0.05 moles or less, particularly preferably 0.01 moles or less, and most preferably 0.005 moles or less, relative to 1 mole of the metal iron.

When the content of Cu contained in the Cu compound is 0.00001 moles or more relative to 1 mole of the metal iron, the influence of impurities on the deactivation of the Cu can be effectively suppressed. Also, when the content of Cu contained in the Cu compound is 5 moles or less relative to 1 mole of the metal iron, a decrease in the productivity of the iron carboxylate or a decrease in the purity of the product can be effectively prevented.

The Cu compound used in an exemplary embodiment of the present invention may be in a state of being dissolved in the reaction liquid, or may be in a state of not being dissolved; however, a dissolved state is preferred.

There are no particular limitations on the Cu compound used in an exemplary embodiment of the present invention;

however, the Cu compound is preferably a compound containing one kind of metal. The Cu compound used in an exemplary embodiment of the present invention is preferably a compound having Cu and a ligand. The ligand is preferably an ionic ligand.

Examples of the ligand include acetate ion, methacrylate ion, acrylate ion, acetylacetonate ion, formate ion, propionate ion, oxalate ion, malonate ion, succinate ion, adipate ion, fumarate ion, maleate ion, pyruvate ion, citrate ion, I$^-$, Br$^-$, Cl$^-$, F$^-$, sulfate ion, nitrate ion, and azide ion.

Examples of the Cu compound include cupper methacrylate, copper acrylate, copper acetylacetonate, copper chloride, copper bromide, copper iodide, and copper nitrate. In addition to them, hydrates, amine adducts and the like of these metal compounds may also be included.

Examples of the anion that satisfies the condition (D) include I$^-$, Br$^-$, Cl$^-$, sulfate ion, nitrate ion, trifluoromethanesulfonate ion, trifluoroacetate ion, maleate ion, and oxalate ion. The pKa according to the condition (D) of trifluoroacetate ion or the like is 1 or less, which is more preferred; the pKa of nitrate ion or the like is 0 or less, which is particularly preferred; and the pKa of I$^-$, Br$^-$, Cl$^-$, sulfate ion, trifluoromethanesulfonate ion or the like is −2 or less, which is most preferred. Meanwhile, when a protonated form has plural pKa values for one compound, the smallest pKa among them is designated as the pKa according to the condition (D).

Among the anions included in the reaction liquid, the total amount of the anion that satisfies the condition (D) is preferably 0.0005 moles or more, particularly preferably 0.001 moles or more, and most preferably 0.005 moles or more, relative to 1 mole of the metal iron.

Furthermore, among the anions included in the reaction liquid, the total amount of the anion that satisfies the condition (D) is more preferably 1 mole or less, even more preferably 0.1 moles or less, particularly preferably 0.05 moles or less, and most preferably 0.01 moles or less, relative to 1 mole of the metal iron.

When the total amount of the anion that satisfies the condition (D) included in the reaction liquid is 0.0001 moles or more relative to 1 mole of the metal iron, a passive state is not easily formed, and the iron carboxylate can be produced without significantly decreasing the reaction rate. Also, when the total amount is 10 moles or less relative to 1 mole of the metal iron, the amount of the protonated form of anion generated by an equilibrium reaction between the anion and the carboxylic acid is reduced, and generation of hydrogen can be suppressed.

The iron carboxylate produced in the present exemplary embodiment is a compound having an iron-carboxylate bond that is obtainable from a carboxylic acid and metal iron, and examples thereof include a compound represented by the following Formula (2). Meanwhile, the iron carboxylate may have adducts of water, an amine compound, a nitrile compound and the like.

[Chemical Formula 2]

$$Fe_aO_bX_cL_d \quad (2)$$

wherein in Formula (2), Fe represents trivalent iron or divalent iron, and preferably trivalent iron; a represents an integer from 1 to 4, and preferably 1 or 3; b represents an integer from 0 to 4, and preferably 0 or 1; c represents an integer from 0 to 4, and preferably 0 or 1; d represents an integer from 1 to 8, and preferably 1, 3, 6 or 7;

X represents a ligand selected from the group consisting of OH$^-$, Cl$^-$, F$^-$, I$^-$, Br$^-$, SO$_4^{2-}$, NO$_3^-$, ClO$_4^-$, PF$_6^-$, BF$_4^-$, R$^5$—(SO$_3^-$)$_n$, R$^5$—(PO$_3^-$)$_n$ and the like; R$^5$ represents a linear, branched or cyclic alkyl group having 1 to 20 carbon atoms that is optionally selectively substituted; a linear, branched or cyclic aryl group having 1 to 20 carbon atoms that is optionally selectively substituted; or a hydrogen atom; n represents an integer from 1 to 4; and L represents a ligand represented by the following Formula (3):

[Chemical Formula 3]

$$R^6(COO^-)_m \quad (3)$$

wherein in Formula (3), m represents an integer from 1 to 10, preferably an integer from 1 to 4, particularly preferably 1 or 2, and most preferably 1; R$^6$ represents a hydrogen atom, a halogen atom, or a group having 1 to 50 carbon atoms, and R$^6$ may have one or more of a double bond, a triple bond, an ester bond, an amide bond, an ether bond, a sulfide bond, a disulfide bond, a urethane bond, an amino group, a nitro group, a cyano group, a thiol group, a hydroxyl group, a ketone group, a formyl group, an acetal group, a thioacetal group, a sulfonyl group, a halogen atom, a silicon atom, or a phosphorus atom, or may have a cyclic structure or an aromatic structure.

According to the present exemplary embodiment, various forms of Fe in Formula (2) may be identical or different. Therefore, the expression "Fe represents trivalent iron or divalent iron" described in the present specification is equivalent to the expression "various forms of Fe independently represent trivalent iron or divalent iron".

The iron carboxylate produced by the method related to the present invention may be produced as a mixture of compound having an iron-carboxylate bond.

When the iron carboxylate produced in the present exemplary embodiment has a structure containing Fe(III), since the reaction is accelerated when carried out in an oxygen-containing gas atmosphere such as oxygen or air, it is preferable to carry out the reaction in an oxygen-containing gas atmosphere. The oxygen-containing gas may be introduced directly to the reaction liquid, or may be introduced from two or more sites of the reaction vessel.

The form of the reaction vessel used in the present exemplary embodiment is not particularly limited, and for example, a batch type reaction vessel, a continuous flow stirred reaction vessel, and a plug flow reaction vessel can be used. Among them, a batch type reaction vessel and a continuous flow stirred reaction vessel in which the change in the fluid volume caused by generated gases is small, and the design can be simplified, are preferred, and a batch type reaction vessel is more preferred. Furthermore, the reaction vessel used in the present exemplary embodiment may have baffle plates or structures in the inside in order to increase the efficiency of stirring.

The iron carboxylate or the iron carboxylate-containing solution prepared in this manner can be used as a catalyst for various chemical reactions singly or as a mixture with other kinds of metals. Examples of the chemical reactions include a coupling reaction, a transesterification reaction, an esterification reaction, hydroesterification, hydroformylation, a hydrogenation reaction, an oxidation reaction, a reduction reaction, and an addition reaction to a carboxylic acid. Particularly, the iron carboxylate or the iron carboxylate-containing solution can be used as a catalyst preferable for an addition reaction of an alkylene oxide to a carboxylic acid, and a carboxylic acid hydroxyalkyl ester is produced.

The alkylene oxide used in the production of the carboxylic acid hydroxyalkyl ester is not particularly limited, and may contain atoms of halogens, nitrogen (N), sulfur (S), oxygen (O), silicon (Si) and the like within the molecule. Furthermore, the alkylene oxide is preferably an alkylene oxide having 2 to 15 carbon atoms, and from the viewpoint of reactivity, an alkylene oxide having 2 to 6 carbon atoms is more preferred. Ethylene oxide (oxidized ethylene), propylene oxide, 1,2-butylene oxide, 2,3-butylene oxide, and isobutylene oxide are even more preferred; ethylene oxide and propylene oxide are particularly preferred; and ethylene oxide is most preferred.

The carboxylic acid used in the production of the carboxylic acid hydroxyalkyl ester is not particularly limited, and the number of carboxyl groups in the molecule may be one or two or more. Examples of the carboxylic acid include formic acid, acetic acid, propionic acid, butyric acid, oxalic acid, malonic acid, succinic acid, glutaric acid, adipic acid, fumaric acid, maleic acid, pyruvic acid, acrylic acid, methacrylic acid, and crotonic acid. Among these, acrylic acid and methacrylic acid are preferred. The carboxylic acids may be used singly, or two or more kinds may be used as mixtures.

In the production of the carboxylic acid hydroxyalkyl ester, the ratio of the carboxylic acid and the alkylene oxide is not particularly limited; however, from the viewpoint of productivity, the molar ratio of the carboxylic acid and the alkylene oxide (carboxylic acid having n carboxyl groups (wherein n represents an integer of 1 or more) in one molecule/alkylene oxide) is preferably 0.1/n to 10/n, more preferably 0.5/n to 3/n, even more preferably 0.7/n to 1.8/n, and particularly preferably 0.85/n to 1.3/n. In the production of the carboxylic acid hydroxyalkyl ester, the molar ratio of the carboxylic acid and the alkylene oxide (carboxylic acid having n carboxyl groups (wherein n represents an integer of 1 or more) in one molecule/alkylene oxide) in one molecule/alkylene oxide) in the case of including at least one metal selected from the group consisting of Ag, Bi and Pd, or a metal compound containing the relevant metal, is preferably 0.1/n to 10/n, more preferably 0.35/n to 3/n, even more preferably 0.6/n to 1.8/n, and particularly preferably 0.75/n to 1.3/n.

Among the carboxylic acids used in the production of the carboxylic acid hydroxyalkyl ester, the amount of the carboxylic acid having n carboxyl groups (wherein n represents an integer of 1 or larger) in one molecule is not particularly limited; however, the amount is preferably 10/n moles or more, more preferably 20/n moles or more, even more preferably 50/n moles or more, and particularly preferably 100/n moles or more, relative to 1 mole of the iron carboxylate. The amount of the carboxylic acid is preferably 1,000,000/n moles or less, more preferably 100,000/n moles or less, even more preferably 10,000/n moles or less, and particularly preferably 1000/n moles or less, relative to 1 mole of the iron carboxylate. When the amount of the carboxylic acid is 10/n moles or more relative to 1 mole of the metal iron, the reaction can be carried out without having any iron carboxylate precipitated. Furthermore, when the amount of the carboxylic acid is 1,000,000/n moles or less, the proportion of unreacted carboxylic acid caused by deactivation of the iron carboxylate can be reduced.

The reaction temperature in the production of the carboxylic acid hydroxyalkyl ester is preferably 0° C. to 180° C., more preferably 30° C. to 150° C., even more preferably 40° C. to 120° C., and particularly preferably 50° C. to 100° C., from the viewpoints of the reaction rate and the suppression of side reactions.

When the carboxylic acid used in the production of the carboxylic acid hydroxyalkyl ester has a double bond, it is preferable to perform the reaction in the co-presence of a polymerization inhibitor, and any known polymerization inhibitor can be used. For example, the polymerization inhibitors listed as examples in relation to the above-described method for producing the iron carboxylate can be used.

In the production of the carboxylic acid hydroxyalkyl ester, any one or two or more kinds of ammonium salts, amine compounds, phosphonium salts, phosphine compounds and the like may be further incorporated and used as a catalyst, in addition to the iron carboxylate produced by the present exemplary embodiment.

EXAMPLES

Hereinafter, the present invention will be described in detail by way of Examples, but the present invention is not intended to be limited to these. Meanwhile, the analysis of hydrogen gas and the analysis of 2-hydroxyethyl methacrylate and the like in the Examples were carried out using gas chromatography (GC).

Example 1

In a 300-mL three-necked flask equipped with a gas inlet tube, 0.837 g (15.0 mmol) of an iron powder (atomized iron powder, manufactured by Wako Pure Chemical Industries, Ltd., median diameter: 82.0 µm) and 0.065 g (0.29 mmol in terms of trivalent iron) of iron(III) acetate (Fe: 25% by mass) were introduced, and then 200.1 g (3.33 mol) of acetic acid was introduced therein. While air was bubbled into this solution at a flow rate of 75.7 mL/min, the solution was stirred using a stirrer tip and was heated to 110° C. using an oil bath, and the solution was maintained for 190 minutes. Then, the iron powder disappeared, and a red-brown precipitate was precipitated. The acetic acid in the reaction liquid thus obtained was removed using an evaporator, subsequently 150 mL of hexane was added thereto to suspend the residue, and a solid precipitated therefrom was separated by filtration. The product thus obtained was dried using a vacuum pump, and thus 3.12 g of iron(III) acetate was obtained. Also, the total amount of hydrogen generated during heating was 0.081 mmol.

Comparative Example 1

The operation was carried out in the same manner as in Example 1, except that iron(III) acetate was not added. As a result, 3.03 g of iron(III) acetate was obtained. Also, the total amount of hydrogen generated during heating was 0.108 mmol.

Example 2

In a 300-mL three-necked flask equipped with a gas inlet tube, 0.558 g (10.0 mmol) of an iron powder (atomized iron powder, manufactured by Wako Pure Chemical Industries, Ltd., median diameter: 82.0 µm), 0.388 g (1.1 mmol in terms of trivalent iron) of Fe(acac)$_3$, 225.3 g (2.62 mol) of methacrylic acid, and 0.099 g of 4-hydroxy-2,2,6,6-tetramethylpiperidin-N-oxyl (HO-TEMPO) as a polymerization inhibitor were introduced. While air and nitrogen were separately bubbled into this solution at a flow rate of 10.0 mL/min of air and 70.0 mL/min of nitrogen, the solution was stirred using a stirrer tip and was heated to 120° C. using an oil bath, and the solution was maintained for 6.5 hours. Then, the iron powder disappeared, and a red-brown transparent iron(III) methacrylate-containing solution was obtained. In the ultraviolet-visible light absorption spectrum of the solution thus obtained in acetonitrile, a shouldered peak was observed at 342 nm, and a weak absorption was observed at 460 nm. The absorption at 460 nm is generally known to be derived from a trinuclear complex of Fe(III), and thus production of a trinuclear complex of iron(III) methacrylate was confirmed. The concentration of iron(III) methacrylate in the solution detected from the UV spectrum was 0.049 mol/L in terms of Fe concentration. Also, the total amount of hydrogen generated during heating was 0.0066 mmol. Meanwhile, the concentration indicated "in terms of Fe concentration" in the description is a concentration as one atom of Fe, and for example, in a case in which the Fe complex thus produced is a mononuclear complex, the Fe concentration has the same value as the molar concentration of the mononuclear complex. In a case in which Fe exists in the form of a trinuclear complex, the Fe concentration has a value triple the molar concentration of the Fe trinuclear complex. Furthermore, in the case of a mononuclear complex and a trinuclear complex, the respective molar concentrations are calculated as Fe concentrations, and the value obtained by summing the Fe concentrations is employed.

Example 3

The operation was carried out in the same manner as in Example 2, except that 0.0867 g (0.54 mmol, 1.08 mmol in terms of trivalent iron) of iron(III) oxide was added instead of adding Fe(acac)$_3$, and the heating and maintenance time was changed from 6.5 hours to 7 hours. For any of the cases before the heating treatment, during the heating treatment, and after the heating treatment, the reaction liquid was in a non-uniform state. After the operation, this reaction liquid was filtered through a filter having a pore size of 0.45 μm, and an iron(III) methacrylate-containing solution having a Fe concentration of 0.044 mol/L was obtained. At this time, the total amount of hydrogen generated during heating was 0.0101 mmol.

Comparative Example 2

The operation was carried out in the same manner as in Example 3, except that iron(III) oxide (Fe$_2$O$_3$) was not added. As a result, an iron(III) methacrylate-containing solution having a Fe concentration of 0.045 mol/L was obtained. At this time, the total amount of hydrogen generated during heating was 0.0133 mmol.

Example 4

The operation was carried out in the same manner as in Comparative Example 2, except that only air was bubbled into the solution at a flow rate of 10.0 mL/min, instead of separately bubbling air at a flow rate of 10.0 mL/min and nitrogen at a flow rate of 70.0 mL/min. As a result, an iron(III) methacrylate-containing solution (hereinafter, solution A) having a Fe concentration of 0.046 mol/L was obtained.

In another 300-mL three-necked flask equipped with an air inlet tube, 0.557 g (10.0 mmol) of an iron powder (atomized iron powder, manufactured by Wako Pure Chemical Industries, Ltd., median diameter: 82.0 μm), 25.2 g (1.5 mmol in terms of trivalent iron) of the solution A, 200.3 g (2.33 mol) of methacrylic acid, and 0.104 g of HO-TEMPO as a polymerization inhibitor were introduced. While air and nitrogen were separately bubbled into this solution at a flow rate of 10.0 mL/min for air and 70.0 mL/in for nitrogen, the solution was stirred with a stirring tip and was heated to 120° C. in an oil bath, and the solution was maintained for 7.3 hours. As a result, an iron(III) methacrylate solution having a Fe concentration of 0.050 mol/L was obtained. At this time, the total amount of hydrogen generated during heating was 0.0068 mmol.

Example 5

In a 500-mL four-necked flask equipped with a gas inlet tube, 1.166 g (20.9 mmol) of an iron powder (electrolytic iron powder, manufactured by Wako Pure Chemical Industries, Ltd., median diameter: 52.5 μm), 0.117 g (0.5 mmol in terms of trivalent iron) of iron(III) methacrylate (Fe: 23.1% by mass), 450.0 g (5.29 mol) of methacrylic acid, and 0.023 g of hydroquinone (HQ) as a polymerization inhibitor were introduced. While air and nitrogen were separately bubbled into this solution at a flow rate of 19.9 mL/min for air and 55.2 mL/in for nitrogen, the solution was stirred with a stirring tip and was heated to 120° C. using an oil bath, and the solution was maintained for 5.5 hours. As a result, an iron(III) methacrylate solution having a Fe concentration of 0.050 mol/L was obtained (solution B). At this time, the total amount of hydrogen generated during heating was 0.172 mmol.

Comparative Example 3

The operation was carried out in the same manner as in Example 5, except that iron(III) methacrylate (Fe: 23.1% by mass) was not added. As a result, an iron(III) methacrylate solution having a Fe concentration of 0.045 mol/L was obtained. At this time, the total amount of hydrogen generated during heating was 0.214 mmol.

Example 6

A mixed solution (solution C) of 2.79 g (0.019 mol) of choline chloride and 0.93 g (0.049 mol) of water was prepared at room temperature. Furthermore, a solution (solution D) of 2.98 g (0.020 mol) of triethanolamine and 0.053 g of a benzyl ester form of HO-TEMPO as a polymerization inhibitor dissolved in 61.0 g (0.709 mol) of methacrylic acid (MAA) was prepared at room temperature. Subsequently, the solution C and the solution D were introduced into a I-L pressurized reactor made of SUS, and then 425.0 g of the solution B introduced into the pressurized reactor made of SUS. While this mixed solution was stirred, 30 g (0.68 mol) of ethylene oxide (EO) was added dropwise thereto over 7 minutes at 30° C., and subsequently, 290 g (6.58 mol) of EO was added dropwise thereto over 110 minutes at 66° C. This reaction liquid was stirred for 4 hours at 66° C., and then was cooled to 50° C. The EO remaining in the reaction liquid was removed under reduced pressure (11.3 kPa) over 1.5 hours. From a GC analysis of the reaction liquid obtained in this manner, it was found that the reaction yield of 2-hydroxyethyl methacrylate was 90.9% (on the basis of the moles of the raw material methacrylic acid), the amount of residual methacrylic acid in the liquid was 0.4% by mass, the amount of ethylene glycol dimethacrylate produced as a side product was 5.6% by mass, and the amount of diethylene glycol monomethacrylate was 4.9% by mass.

Example 11

In a 300-mL three-necked flask equipped with a gas inlet tube, 0.0374 g (0.16 mmol) of tin(II) acetate and 250.0 g (4.16 mol) of acetic acid were introduced, and then 2.20 g (39.4 mmol) of an iron powder (atomized iron powder, manufactured by Wako Pure Chemical Industries, Ltd., median diameter ($D_{50}$): 82.0 µm) was introduced therein. While air was caused to flow into the upper space of this reaction liquid at a rate of 90.0 mL/min, the reaction liquid was stirred with a stirrer tip and was heated to 95° C. using an oil bath, and the reaction liquid was maintained for 5.4 hours. Then, the iron powder disappeared, and a red-brown precipitate was precipitated. Subsequently, the acetic acid contained in the reaction liquid was removed with an evaporator, and then 150 mL of hexane was added to the reaction liquid to suspend the residue. A solid precipitated therefrom was obtained by filtration. The solid thus obtained was dried using a vacuum pump, and as a result, 8.49 g of iron(iii) acetate was obtained. Furthermore, the exit gas was analyzed by gas chromatography during heating, and the total amount of hydrogen generated was 0.146 mmol.

Examples 12 to 17 and Comparative Examples 11 and 12

The operation was carried out in the same manner as in Example 11, except that the metal compounds and conditions indicated in Table 1 were used. The mass of iron(III) acetate thus obtained and the total amount of hydrogen generated are also described together in Table 1. Meanwhile, Sn(OAc)$_2$ in the table represents tin(II) acetate, Cr(OAc)$_3$ represents chromium(III) acetate, Mn(acac)$_2$ represents manganese(II) bisacetylacetonate, Zr(acac)$_4$ represents zirconium(IV) tetrakisacetylacetonate, and RuCl$_3$ represents ruthenium(III) chloride. The median diameter ($D_{50}$) of Ni powder was 72 µm.

Example 21

In a 500-mL four-necked flask equipped with a gas inlet tube, 1.167 g (20.9 mmol) of an iron powder (electrolytic iron powder, manufactured by Wako Pure Chemical Industries, Ltd., median diameter: 52.5 µm), 0.0244 g (0.083 mmol) of nickel acetylacetonate dihydrate, 450.0 g (5.29 mol) of methacrylic acid, and 0.1000 g of 4-hydroxy-2,2,6, 6-tetramethylpiperidin-N-oxyl (HO-TEMPO) as a polymerization inhibitor were introduced. While air and nitrogen were separately bubbled into this solution at a flow rate of 19.9 mL/min for air and 55.2 mL/in for nitrogen, the solution was stirred with a stirring tip and was heated to 120° C. using an oil bath, and the solution was maintained for 5.4 hours. Then, the iron powder disappeared, and a red-brown transparent iron(III) methacrylate-containing solution was obtained.

In the ultraviolet-visible light absorption spectrum of the solution thus obtained in acetonitrile, a shouldered peak was observed at 342 nm, and a weak absorption was observed at 460 nm. The absorption at 460 nm is generally known to be derived from a trinuclear complex structure of Fe(III), and thus the production of a trinuclear complex of iron(III) methacrylate was confirmed. The concentration of iron(III) methacrylate in the solution detected from the UV spectrum was 0.05 mol/L as the Fe concentration. Furthermore, the total amount of hydrogen generated during heating was 0.078 mmol.

Examples 22 to 29 and Comparative Examples 21 to 24

The operation was carried out in the same manner as in Example 21, except that the metal compounds and conditions indicated in Table 2 were used. The total amount of hydrogen generated, the Fe concentration of the reaction liquid thus obtained, and the presence or absence of the disappearance of iron powder in the purified liquid at the time of completion of the reaction are also described together in Table 2. Meanwhile, Ni(acac)$_2$ represents nickel (II) bisacetylacetonate, Ni(OAc)$_2$ represents nickel(II) acetate, Pb(C$_6$H$_8$O$_7$) represents lead(III) citrate, MoO$_2$ (acac)$_2$ represents bis(acetylacetonato)molybdenum(IV) dioxide, Co(OAc)$_2$ represents cobalt(II) acetate, CdCl$_2$ represents cadmium(II) chloride, Na(MAA) represents sodium methacrylate, and Cu(OAc)$_2$ represents copper(II) acetate. The median diameter ($D_{50}$) of Ni powder was 72 µm.

Example 31

The operation was carried out in the same manner as in Example 27, except that 0.038 g (0.35 mmol) of tetramethylammonium chloride was further added to the solution before heating, and the heating time was changed to 5.0 hours. At this time, Cl ions were present in the reaction solution, and the pKa of the protonated form thereof was −6.1. Therefore, the molar ratio of anions whose protonated forms had a pKa of 2 or less/Fe was 0.02. As a result, the iron powder disappeared, and a red-brown transparent iron(III) methacrylate-containing solution was obtained. The concentration of iron(III) methacrylate in the solution was 0.05 mol/L in terms of Fe concentration, and the total amount of hydrogen generated during heating was 0.126 mmol.

Example 32

The operation was carried out in the same manner as in Example 27, except that 0.0074 g (0.068 mmol) of tetramethylammonium chloride was further added to the solution before heating. At this time, Cl ions were present in the reaction solution, and the pKa of the protonated form thereof was −6.1. Therefore, the molar ratio of anions whose protonated forms had a pKa of 2 or less/Fe was 0.003. As a result, the iron powder disappeared, and a red-brown transparent iron(III) methacrylate-containing solution was obtained. The concentration of iron(III) methacrylate in the solution was 0.05 mol/L in terms of Fe concentration, and the total amount of hydrogen generated during heating was 0.102 mmol.

Example 41

A mixed solution (solution C) of 2.79 g (0.019 mol) of choline chloride and 0.93 g (0.049 mol) of water was prepared at room temperature. Furthermore, a solution (solution D) of 2.98 g (0.020 mol) of triethanolamine and 0.053 g of a benzyl ester form of HO-TEMPO as a polymerization inhibitor dissolved in 61.0 g (0.709 mol) of methacrylic acid (MAA) was prepared at room temperature. Subsequently, the solution C and the solution D were introduced into a 1-L pressurized reactor made of SUS, and then 427.9 g of the iron(III) methacrylate solution obtained in Example 21 was introduced into the pressurized reactor made of SUS. While this mixed solution was stirred, 30 g (0.68 mol) of ethylene oxide (EO) was added dropwise thereto over 7 minutes at 30° C., and subsequently, 300 g (6.81 mol) of EO was added dropwise thereto over 115 minutes at 66° C. This reaction liquid was stirred for 3.5 hours at 66° C., and then was cooled to 50° C. The EO remaining in the reaction liquid was removed under reduced pressure (11.3 kPa) over 1.5 hours. As a result, a 2-hydroxyethyl methacrylate solution in which the amount of residual methacrylic acid in the liquid was 0.4% by mass, the amount of ethylene glycol dimethacrylate produced as a side product was 1.0% by mass, and the amount of diethylene glycol monomethacrylate was 5.4% by mass, was obtained. At this time, the reaction yield of 2-hydroxyethyl methacrylate was 93.9% (on the basis of the moles of the raw material methacrylic acid).

Example 42

The operation was carried out in the same manner as in Example 31, except that 428.4 g of the iron(III) methacrylate solution obtained in Example 27 was added instead of adding the iron(III) methacrylate solution obtained in Example 21, and the amount of EO dropped at 66° C. was changed to 280 g. As a result, a 2-hydroxyethyl methacrylate solution in which the amount of residual methacrylic acid in the liquid was 0.5% by mass, the amount of the ethylene glycol dimethacrylate produced as a side product was 0.1% by mass, and the amount of diethylene glycol monomethacrylate was 5.1% by mass, was obtained. At this time, the reaction yield of 2-hydroxyethyl methacrylate was 86.8% (on the basis of the moles of the raw material methacrylic acid).

Example 51

In a 500-mL four-necked flask equipped with a gas inlet tube, 0.8378 g (15.0 mmol) of an iron powder (electrolytic iron powder, manufactured by Wako Pure Chemical Industries, Ltd., median diameter: 52.5 μm), 0.0100 g (0.045 mmol) of palladium(II) acetate, 260.0 g (3.06 mol) of methacrylic acid, and 0.0200 g of hydroquinone (HQ) as a polymerization inhibitor were introduced. While air and nitrogen were separately bubbled into this solution at a flow rate of 21.6 mL/min for air and 28.4 mL/in for nitrogen, the solution was stirred with a stirring tip and was heated to 120° C. using an oil bath, and the solution was maintained for 5 hours. Then, the iron powder disappeared, and a red-brown transparent iron(III) methacrylate-containing product liquid was obtained.

In the ultraviolet-visible light absorption spectrum of the product liquid thus obtained in acetonitrile, a shouldered peak was observed at 342 nm, and a weak absorption was observed at 460 nm. The absorption at 460 nm is generally known to be derived from a trinuclear complex structure of Fe(III), and thus the production of a trinuclear complex of

TABLE 1

| | Metal or metal compound | | | mol % relative to iron powder | Reaction time (h) | $H_2$ generated (mmol) | Iron acetate (g) | Recognition of iron powder in product liquid |
|---|---|---|---|---|---|---|---|---|
| | Type | Mass (g) | Standard electrode potential of simple metal $M \rightarrow M^{n+}$ | | | | | |
| Example 11 | $Sn(OAc)_2$ | 0.0374 | −0.14 | 0.4 | 5.4 | 0.146 | 8.49 | Disappeared |
| Example 12 | Ni powder (median diameter 72 μm) | 0.0094 | −0.25 | 0.4 | 5.6 | 0.207 | 8.43 | Disappeared |
| Example 13 | Ni powder (median diameter 72 μm) | 0.0019 | −0.25 | 0.1 | 5.3 | 0.320 | 8.38 | Disappeared |
| Example 14 | Ni powder (median diameter 72 μm) | 0.00013 | −0.25 | 0.006 | 4.8 | 0.385 | 8.44 | Disappeared |
| Example 15 | $Cr(OAc)_3$ | 0.0363 | −0.74 | 0.4 | 5.4 | 0.400 | 8.44 | Disappeared |
| Example 16 | $Mn(acac)_3$ | 0.0555 | −1.18 | 0.4 | 5.3 | 0.370 | 8.99 | Disappeared |
| Example 17 | $Zr(acac)_4$ | 0.0770 | −1.53 | 0.4 | 4.7 | 0.363 | 8.53 | Disappeared |
| Comparative Example 11 | None | — | — | — | 5.9 | 0.509 | 8.44 | Disappeared |
| Comparative Example 12 | $RuCl_3 \cdot 2H_2O$ | 0.0379 | 0.46 | 0.4 | 5.0 | 0.626 | 8.51 | Disappeared |

TABLE 2

| | Metal or metal compound | | | mol % relative to iron powder | Reaction time (h) | $H_2$ generated (mmol) | [Fe] of product liquid (M) | Recognition of iron powder in product liquid |
|---|---|---|---|---|---|---|---|---|
| | Type | Mass (g) | Standard electrode potential of simple metal $M \rightarrow M^{n+}$ | | | | | |
| Example 21 | $Ni(acac)_2 \cdot 2H_2O$ | 0.0244 | −0.25 | 0.4 | 5.4 | 0.078 | 0.05 | Disappeared |
| Example 22 | $Ni(OAc)_2 \cdot 4H_2O$ | 0.0215 | −0.25 | 0.4 | 5.5 | 0.083 | 0.05 | Disappeared |
| Example 23 | $Ni(OAc)_2 \cdot 4H_2O$ | 0.0543 | −0.25 | 1.0 | 5.3 | 0.062 | 0.05 | Disappeared |
| Example 24 | $Ni(OAc)_2 \cdot 4H_2O$ | 0.2101 | −0.25 | 4.0 | 5.4 | 0.045 | 0.05 | Disappeared |
| Example 25 | Ni powder (median diameter 72 μm) | 0.0121 | −0.25 | 0.4 | 5.4 | 0.084 | 0.05 | Disappeared |
| Example 26 | $Pb(C_6H_8O_7) \cdot nH_2O$ (56 mass % as Pd) | 0.0310 | −0.13 | 0.4 | 5.1 | 0.075 | 0.05 | Disappeared |
| Example 27 | $MoO_2(acac)_2$ | 0.0273 | −0.20 | 0.4 | 5.4 | 0.097 | 0.05 | Disappeared |
| Example 28 | $Co(OAc)_2$ | 0.0297 | −0.28 | 0.4 | 5.5 | 0.126 | 0.05 | Disappeared |
| Example 29 | $CdCl_2 \cdot 2.5H_2O$ | 0.0187 | −0.40 | 0.4 | 5.2 | 0.131 | 0.05 | Disappeared |
| Comparative Example 21 | None | — | — | — | 5.4 | 0.143 | 0.05 | Disappeared |
| Comparative Example 22 | Na(MAA) | 0.0232 | −2.71 | 1.0 | 5.5 | 0.143 | 0.05 | Disappeared |
| Comparative Example 23 | $Cu(OAc)_2 \cdot H_2O$ | 0.0166 | 0.34 | 0.4 | 6.0 | 0.013 | 0.03 | Remained |
| Comparative Example 24 | Cu powder | 0.0139 | 0.38 | 1.0 | 5.9 | 0.010 | 0.004 | Remained | iron(III) methacrylate was confirmed. The concentration of iron(III) methacrylate in the product liquid detected from the UV spectrum was 0.06 mol/L in terms of Fe concentration. Furthermore, the total amount of hydrogen generated during heating was 0.0044 mmol.

TABLE 3

| | Metal compound | | | $H_2$ generated (mmol) | [Fe] of product liquid (M) | Recognition of iron powder in product liquid |
|---|---|---|---|---|---|---|
| | Type | Mass (g) | mol % relative to iron powder | | | |
| Example 51 | Pd(OAc)$_2$ | 0.0100 | 0.3 | 0.0044 | 0.06 | Disappeared |
| Example 52 | BiO(OAc) | 0.0128 | 0.3 | 0.068 | 0.06 | Disappeared |
| Example 53 | Ag(OAc) | 0.0055 | 0.3 | 0.097 | 0.06 | Disappeared |
| Example 54 | Pd(OAc)$_2$ | 0.0003 | 0.009 | 0.108 | 0.06 | Disappeared |
| Example 55 | Pd(OAc)$_2$ | 0.0027 | 0.08 | 0.033 | 0.06 | Disappeared |
| Example 56 | Pd(OAc)$_2$ | 0.0348 | 1.03 | 0.0010 | 0.06 | Disappeared |
| Comparative Example 51 | None | — | — | 0.121 | 0.06 | Disappeared |
| Comparative Example 52 | Ru(acac)$_3$ | 0.0180 | 0.3 | 0.162 | 0.06 | Disappeared |
| Comparative Example 53 | Rh(OAc)$_2$ | 0.0100 | 0.3 | 0.160 | 0.06 | Disappeared |
| Comparative Example 54 | Ir(acac)$_3$ | 0.0220 | 0.3 | 0.355 | 0.06 | Disappeared |
| Comparative Example 55 | Pt(acac)$_2$ | 0.0055 | 0.09 | 0.472 | 0.06 | Disappeared |
| Comparative Example 56 | CpRe(CO)$_3$ | 0.0046 | 0.09 | 0.122 | 0.06 | Disappeared |

Examples 52 to 56 and Comparative Examples 51 to 56

The operation was carried out in the same manner as in Example 51, except that the metal compounds and conditions indicated in Table 3 were used. The total amount of hydrogen generated, the Fe concentration of the reaction liquid thus obtained, and the presence or absence of the disappearance of iron powder in the product liquid at the time of completion of the reaction were described together in Table 1. Meanwhile, Pd(OAc)$_2$ in the table represents palladium(II) acetate, BiO(OAc) represents bismuth(III) acetate oxide, Ag(OAc) represents silver(I) acetate, Ru(acac)$_3$ represents tris(acetylacetonato)ruthenium(III), Rh(OAc)$_2$ represents rhodium(II) acetate, Ir(acac)$_3$ represents tris(acetylacetonato)iridium(III), Pt(acac)$_2$ represents bis(acetylacetonato)platinum(II), and CpRe(CO)$_3$ represents cyclopentadienylrhenium(I) tricarbonyl.

Examples 57 to 59

The operation was carried out in the same manner as in Example 51, except that the metal compounds and the conditions indicated in Table 4 were used, and tetramethylammonium chloride was added to the solution before heating. The Fe concentration of the product liquid thus obtained, and the presence or absence of the disappearance of iron powder in the product liquid at the time of completion of the reaction are also described in Table 4.

Example 60

The operation was carried out in the same manner as in Example 51, except that 0.0059 g (0.044 mmol) of copper (II) chloride (CuCl$_2$) was used instead of using palladium(II) acetate. At this time, Cl ions were present in the reaction solution, and the pKa of the protonated form thereof was −6.1. Therefore, the molar ratio of anions whose protonated forms have a pKa of 2 or less/Fe was 0.006. As a result, the iron powder disappeared, and a red-brown transparent iron (III) methacrylate-containing product liquid was obtained. The concentration of iron(III) methacrylate in the product liquid was 0.06 mol/L in terms of Fe concentration, and the total amount of hydrogen generated during heating was 0.067 mmol.

Comparative Example 57

The operation was carried out in the same manner as in Example 51, except that 0.0090 g (0.045 mmol) of copper (II) acetate.monohydrate (Cu(OAc)$_2$.H$_2$O) was used instead of using palladium(II) acetate, and the heating and maintenance time was changed from 5 hours to 6 hours. At this time, the molar ratio of anions whose protonated forms had a pKa of 2 or less/Fe in the reaction solution was 0. As a result, the iron powder did not disappear, and the concentration of iron(iii) methacrylate in the product liquid was 0.01 mol/L in terms of Fe concentration.

Example 61

In a 50-mL pressurized reactor made of SUS, 7.5 g of the iron(III) methacrylate-containing product liquid obtained in

TABLE 4

| | Metal compound | | | Tetramethylammonium chloride | | $H_2$ generated (mmol) | [Fe] of product liquid (M) | Recognition of iron powder in product liquid |
|---|---|---|---|---|---|---|---|---|
| | Type | Mass (g) | mol % relative to iron powder | Mass (g) | mol % relative to iron powder | | | |
| Example 57 | Pd(OAc)$_2$ | 0.0101 | 0.30 | 0.0015 | 0.1 | 0.013 | 0.06 | Disappeared |
| Example 58 | Pd(OAc)$_2$ | 0.0348 | 1.03 | 0.0315 | 2.0 | 0.021 | 0.06 | Disappeared |
| Example 59 | Pd(OAc)$_2$ | 0.0100 | 0.30 | 0.1748 | 10.6 | 0.115 | 0.06 | Disappeared |

Example 51 (methacrylic acid: 87 mmol), 6.6 g (114 mmol) of propylene oxide, and 0.002 g of 4-hydroxy-2,2,6,6-tetramethylpiperidin-N-oxyl as a polymerization inhibitor were introduced. This solution was stirred with a stirrer tip and was heated to 70° C., and the solution was maintained for 3.5 hours. Subsequently, the solution was immediately cooled to 0° C. in ice water. As a result, the methacrylic acid in the liquid disappeared, and the reaction yield of 2-hydroxypropyl methacrylate was 72.5% (on the basis of the moles of the raw material methacrylic acid), while the reaction yield of 1-hydroxypropyl methacrylate was 23.7% (on the basis of the moles of the raw material methacrylic acid).

TABLE 5

| | Iron methacrylate solution | Residual ratio (%) of methacrylic acid | 2HPMA yield (%) | 1HPMA yield (%) | Total yield of HPMA (%) |
|---|---|---|---|---|---|
| Example 61 | Product liquid of Example 51 | 0 | 72.5 | 23.7 | 96.2 |
| Example 62 | Product liquid of Example 54 | 0 | 67.3 | 28.6 | 95.9 |
| Example 63 | Product liquid of Example 55 | 0 | 67.0 | 29.3 | 96.3 |

Examples 62 and 63

The operation was carried out in the same manner as in Example 61, except that the iron(III) methacrylate-containing product liquids indicated in Table 5 were used. The residual ratio of methacrylic acid of the reaction liquid thus obtained, and the reaction yields of 2-hydroxypropyl methacrylate and 1-hydroxypropyl methacrylate (on the basis of the moles of the raw material methacrylic acid) are also described in Table 3. Meanwhile, MAA in the table represents methacrylic acid, 2HPMA represents 2-hydroxypropyl methacrylate, and 1HPMA represents 2-hydroxypropyl methacrylate.

The invention claimed is:

1. A method for producing an iron carboxylate, the method comprising:
    reacting metal iron with at least one carboxylic acid selected from the group consisting of acrylic acid and methacrylic acid in a reaction liquid at a temperature of 110° C.-150° C.,
    wherein:
    the reaction liquid comprises a metal other than iron having a standard electrode potential of from −2.5 to 0.1, or a metal compound comprising the relevant metal; or
    the reaction liquid comprises at least one metal selected from the group consisting of Ag, Bi and Pd, or a metal compound comprising the relevant metal.

2. The method according to claim 1,
    wherein the reaction liquid comprises a metal other than iron having a standard electrode potential of from −2.5 to 0.1, or a metal compound comprising the relevant metal, and wherein a content of the metal other than iron having a standard electrode potential of −2.5 to 0.1 in the reaction liquid is from 0.00001 moles to 5 moles relative to 1 mole of the metal iron, or a content of the metal compound comprising the metal other than iron having a standard electrode potential of −2.5 to 0.1 in the reaction liquid is an amount such that the amount of the metal comprised in the metal compound is from 0.00001 moles to 5 moles relative to 1 mole of the metal iron.

3. The method according to claim 1,
    wherein the reaction liquid comprises a metal other than iron having a standard electrode potential of from −2.5 to 0.1, or a metal compound comprising the relevant metal, and the standard electrode potential of the metal is from −0.44 to 0.

4. The method according to claim 2,
    wherein the reaction liquid comprises a metal compound comprising a metal other than iron having a standard electrode potential of from −2.5 to 0.1; and
    wherein a total amount of an anion that is comprised in the reaction liquid and has a protonated form having a pKa, which is a negative common logarithm of an acid dissociation constant, in water at 25° C. of 2 or less is 10 moles or less relative to 1 mole of the metal iron in the reaction liquid.

5. The method according to claim 2,
    wherein the reaction liquid comprises a metal compound comprising a metal other than iron having a standard electrode potential of from −2.5 to 0.1; and
    wherein the metal compound is an organometallic compound comprising the metal and an ionic ligand.

6. The method according to claim 1,
    wherein the reaction liquid comprises at least one metal selected from the group consisting of Ag, Bi and Pd, or a metal compound comprising the relevant metal and wherein a content of the at least one metal selected from the group consisting of Ag, Bi and Pd in the reaction liquid is from 0.00001 moles to 5 moles relative to 1 mole of the metal iron, or a content of the metal compound comprising the at least one metal selected from the group consisting of Ag, Bi and Pd in the reaction liquid is an amount such that the amount of the metal comprised in the metal compound is from 0.00001 moles to 5 moles relative to 1 mole of the metal iron.

7. The method according to claim 6,
    wherein the reaction liquid comprises at least one metal compound comprising a metal selected from the group consisting of Ag, Bi and Pd, and
    wherein a total amount of an anion that is comprised in the reaction liquid and has a protonated form having a pKa, which is a negative common logarithm of an acid dissociation constant, in water at 25° C. of 2 or less, is 10 moles or less relative to 1 mole of the metal iron in the reaction liquid.

8. The method according to claim 6,
    wherein the reaction liquid comprises at least one metal compound comprising a metal selected from the group consisting of Ag, Bi and Pd, and the at least one metal compound is an organometallic compound comprising the metal and an ionic ligand.

9. A method for producing an iron carboxylate, the method comprising:
    reacting a metal iron with at least one carboxylic acid selected from the group consisting of acrylic acid and methacrylic acid in a reaction liquid at a temperature of 110° C.-150° C., wherein the reaction liquid comprises a Cu compound in an amount such that the amount of Cu comprised in the Cu compound is from 0.00001 moles to 5 moles relative to 1 mole of the metal iron; and the reaction liquid comprises an anion, whose protonated form has a pKa, which is a negative common logarithm of an acid dissociation constant, in water at 25° C. of 2 or less, in an amount f from 0.0001 moles to 10 moles relative to 1 mole of the metal iron.

10. The method according to claim 1, wherein the iron carboxylate is an iron carboxylate comprising trivalent iron.

11. The method according to claim 1, further comprising introducing an oxygen-comprising gas into the reaction liquid.

12. The method according to claim 1, wherein:
the reaction liquid comprises a metal other than iron having a standard electrode potential of from −2.5 to 0.1, or a metal compound comprising the relevant metal.

13. The method according to claim 1, wherein:
the reaction liquid comprises at least one metal selected from the group consisting of Ag, Bi and Pd, or a metal compound comprising the relevant metal.

14. The method according to claim 1, comprising:
reacting said metal iron with said at least one carboxylic acid selected from the group consisting of acrylic acid and methacrylic acid in a reaction liquid at a temperature of 120° C.-150° C.

15. The method according to claim 1, comprising:
reacting said metal iron with methacrylic acid in a reaction liquid at a temperature of 120° C.-150° C.

16. The method according to claim 9, comprising:
reacting said metal iron with said at least one carboxylic acid selected from the group consisting of acrylic acid and methacrylic acid in a reaction liquid at a temperature of 120° C.-150° C.

* * * * *